United States Patent
Fix et al.

(10) Patent No.: US 9,418,857 B2
(45) Date of Patent: Aug. 16, 2016

(54) SENSOR COMPONENT FOR A GAS AND/OR LIQUID SENSOR, PRODUCTION METHOD FOR A SENSOR COMPONENT FOR A GAS AND/OR LIQUID SENSOR, AND METHOD FOR DETECTING AT LEAST ONE MATERIAL IN A GASEOUS AND/OR LIQUID MEDIUM

(71) Applicants: Richard Fix, Gerlingen (DE); Bernd Schumann, Rutesheim (DE)

(72) Inventors: Richard Fix, Gerlingen (DE); Bernd Schumann, Rutesheim (DE)

(73) Assignee: ROBERT BOSCH GMBH, Stuttgart (DE)

( * ) Notice: Subject to any disclaimer, the term of this patent is extended or adjusted under 35 U.S.C. 154(b) by 242 days.

(21) Appl. No.: 14/313,569

(22) Filed: Jun. 24, 2014

(65) Prior Publication Data

US 2015/0000376 A1    Jan. 1, 2015

(30) Foreign Application Priority Data

Jun. 28, 2013 (DE) .......................... 10 2013 212 735

(51) Int. Cl.
*G01N 7/00* (2006.01)
*H01L 21/304* (2006.01)
*G01N 27/12* (2006.01)

(52) U.S. Cl.
CPC .......... *H01L 21/3043* (2013.01); *G01N 27/128* (2013.01)

(58) Field of Classification Search
CPC .......................... H01L 21/3043; G01N 27/128
USPC ............................................... 73/31.05, 31.06
See application file for complete search history.

(56) References Cited

U.S. PATENT DOCUMENTS

2011/0197657 A1* 8/2011 Gole .................... G01N 27/127
                                                             73/31.05
2011/0263036 A1   10/2011 Blauw et al.

FOREIGN PATENT DOCUMENTS

| DE | 19521984 | 12/1995 |
| DE | 4445359 | 6/1996 |
| DE | 10019010 | 10/2001 |
| DE | 69727001 | 11/2004 |

* cited by examiner

*Primary Examiner* — Walter L Lindsay, Jr.
*Assistant Examiner* — Ruth Labombard
(74) *Attorney, Agent, or Firm* — Norton Rose Fulbright US LLP (57) ABSTRACT

A sensor component is described for a gas and/or liquid sensor having a substrate having at least one first printed conductor and a second printed conductor, which are fashioned such that a voltage can be applied, and having at least one sensitive semiconductor material, additionally including at least one trench a contact segment of the first printed conductor and a contact segment of the second printed conductor being situated on two inner side surfaces at a distance from one another, and the at least one sensitive semiconductor material being filled into the at least one trench in the form of at least one particle, grain, and/or crystal, at least between the first contact segment of the first printed conductor and the first contact segment of the second printed conductor. Also described is a production method for a sensor component for a gas and/or liquid sensor. In addition, also described is a method for detecting at least one material in a gaseous and/or liquid medium.

14 Claims, 7 Drawing Sheets

SENSOR COMPONENT FOR A GAS AND/OR LIQUID SENSOR, PRODUCTION METHOD FOR A SENSOR COMPONENT FOR A GAS AND/OR LIQUID SENSOR, AND METHOD FOR DETECTING AT LEAST ONE MATERIAL IN A GASEOUS AND/OR LIQUID MEDIUM

FIELD OF THE INVENTION

The present invention relates to a sensor component for a gas and/or liquid sensor, and to a gas and/or liquid sensor. The present invention also relates to a production method for a sensor component for a gas and/or liquid sensor, and to a production method for a gas and/or liquid sensor. In addition, the present invention relates to a method for detecting at least one material in a gaseous and/or liquid medium.

BACKGROUND INFORMATION

In German Published Patent Appln. No. 44 45 359, a sensor is described for detecting combustible gases. The sensor includes a substrate having two printed conductors having comb-type interlacing at their head ends. In the area of the interlaced ends, a sensitive semiconducting metal oxide layer is applied over the printed conductors. The sensitive semiconducting metal oxide layer can have a spongelike structure, or can be fashioned as a composite of grains sintered together.

SUMMARY

The present invention creates a sensor component for a gas and/or liquid sensor, a gas and/or liquid sensor, a production method for a sensor component for a gas and/or liquid sensor, a production method for a gas and/or liquid sensor, and a method for detecting at least one material in a gaseous and/or liquid medium.

The subject matters of the present invention have increased sensitivity for at least one detectable material. As explained below in more detail, using the present invention smaller quantities of the at least one material can already be detected in a gaseous and/or liquid medium. In particular, using the present invention lower concentrations of a material can already be reliably measured. The present invention thus contributes to the more reliable detection of the at least one material and/or the more precise determination of its concentration.

Moreover, using the present invention even a comparatively small volume of the medium can be reliably examined for the occurrence of the at least one material or the concentration thereof. Due to the possibility of carrying out such investigations using only a relatively small quantity of the medium, the present invention can advantageously be used for various purposes, for example in fine trace analysis and/or molecular biology. It is also advantageous that due to the small volume a small access channel to the sensor is sufficient for the medium, and a particularly short response time is achieved because the ratio of the volume surrounding the sensor to the channel volume can be made very advantageous. The present invention can however also be used to examine exhaust gases, in medicine, in environmental protection, in consumer protection, and for a large number of further uses. The present invention thus has many possible applications.

Moreover, the present invention realizes gas and/or liquid sensors that need to be equipped only with a comparatively small quantity of the at least one sensitive semiconductor material. Thus, even given the use of a comparatively expensive material as the at least one sensitive semiconductor material, it is still ensured that the gas and/or liquid sensor equipped with a sufficient quantity thereof can be produced at relatively low cost. The present invention thus reduces the costs for a gas and/or liquid sensor and increases the number of materials that can be used therein as the at least one sensitive semiconductor material.

In addition, the present invention offers a possibility for realizing a comparatively small gas and/or liquid sensor. Due to the small constructive space requirement of such a gas and/or liquid sensor, it can be used in many different ways.

Preferably, the two inner side surfaces, parallel to the side of the substrate, contacted by the first contact segment of the first printed conductor and by the first contact segment of the second printed conductor are situated at a distance from one another that is equal to a diameter of the individual particle, grain, or crystal of the at least one sensitive semiconductor material filled into the respective trench, or are larger by at most a factor of 3 than an average diameter of the particles, grains, and/or crystals of the at least one sensitive semiconductor material filled into the at least one trench. In particular, the distance between the two inner side surfaces parallel to the side of the substrate can be greater by at most a factor of 2.5, advantageously at most a factor of 2, preferably at most by a factor of 1.5, than the average diameter of the particles, grains, and/or crystals of the at least one sensitive semiconductor material filled into the at least one trench. As explained in more detail below, such a realization of the sensor component can advantageously increase its sensitivity.

For example, at most a number of ten particles, grains, and/or crystals per trench can be filled into the at least one trench. Here, in particular a trench segment can be designated that results from the multiplication of the trench cross surface by a length of the trench segment, which preferably corresponds approximately to the diameter of the crystals or particles filled in—in particular to the diameter of from approximately 50% to 85% of the filled particles. Specifically, an average number of from one to five particles, grains, and/or crystals, in particular an average number of two to three particles, grains, and/or crystals, can be filled into the at least one trench or into a trench segment as just stated. In this case, even small changes in a concentration of the at least one material can be reliably recognized.

Preferably, at least one surface-active glued and/or adhesive bond is fashioned between a roughened surface of the first contact segment of the first printed conductor and at least one particle, grain, or crystal, contacted thereby, of the at least one sensitive semiconductor material, and/or between a roughened surface of the first contact segment of the second printed conductor and at least one particle, grain, or crystal, contacted thereby, of the at least one sensitive semiconductor material. The adhesive bond can also advantageously result from a bond, achieved in the production process, of the crystals and tilting thereof in the trench structure with elements of the surface roughnesses of the trench structure. In this way, an advantageous hold of the at least one particle, grain, and/or crystal in the respective trench is ensured, as is also a reliable contact between the at least one contact segment and the contacted particle, grain, and/or crystal.

In an advantageous specific embodiment, the at least one sensitive semiconductor material includes tin oxide, zinc oxide, titanium oxide, indium oxide, and/or tungsten oxide. Thus, materials that are easy to sinter can also be used.

Advantageously, the at least one sensitive semiconductor material is doped with tantalum and/or niobium. This ensures a reliably recognizable change in resistance of the at least one sensitive semiconductor material as a response to the contact with the at least one material.

Preferably, the at least one sensitive semiconductor material is doped with at least one alkaline earth metal and/or at least one rare earth metal. In this way, an undesired growth of the particles, grains, and/or crystals of the at least one sensitive semiconductor material can be reliably prevented. In this way, the particles, grains, and/or crystals of the at least one sensitive semiconductor material can be fashioned with a comparatively small average diameter, enabling a good sensitivity of the sensor component.

Moreover, the at least one particle, the at least one grain, and/or the at least one crystal of the at least one sensitive semiconductor material can be coated at least partly with gold, silver, platinum, palladium, rhodium, and/or ruthenium. This ensures in particular a good sensitivity of the sensor component fashioned in this way to particular gases. Likewise, the metal that coats the crystals can be present, in addition to on the surface, also in the interior thereof, e.g. in clusters of from 0.5 to 150 nm, preferably from 1 to 50 nm, and can also be distributed uniformly in the interior, so that according to the present invention no cluster of the outer surface can easily wander into defective places in the interior of the crystal.

In a further advantageous specific embodiment, the at least one trench parallel to the side of the substrate has a U-shaped cross-section, the inner side surfaces with the first contact segment of the first printed conductor and the first contact segment of the second printed conductor being situated on a first limb of the U-shaped cross-section, and a second contact segment of the first printed conductor and a second contact segment of the second printed conductor being fashioned on two further inner side surfaces, situated at a distance from one another, of the at least one trench wall that are situated on a second limb of the U-shaped cross-section. A sensor component fashioned in this way can be fashioned in a relatively simple manner even when there is a comparatively small spacing of the respective inner side surfaces having the associated contact segments.

The advantages enumerated above are also ensured in a gas and/or liquid sensor having such a sensor component.

The advantages can also be realized by carrying out a corresponding production method for a sensor component for a gas and/or liquid sensor. The production method can be developed according to the above-described specific embodiments.

In an advantageous development, after the filling of the at least one particle, the at least one grain, and/or the at least one crystal of the at least one sensitive semiconductor material respectively into the at least one trench, the sensor component is heated to a temperature between 400° C. and 700° C. This ensures the at least one advantageous surface-active glued and/or adhesive bond.

A carrying out of the corresponding production method for a gas and/or liquid sensor also realizes the above-described advantages.

In addition, the above-described advantages can be realized by carrying out the corresponding method for detecting at least one material in a gaseous and/or liquid medium. The method can also be developed in a manner corresponding to the above-described specific embodiments.

BRIEF DESCRIPTION OF THE DRAWINGS

FIGS. 3a and 3b show a top view and a cross-section of a third specific embodiment of the sensor component, FIG. 3b showing a cross-section along the line A-A' of FIG. 3a.

DETAILED DESCRIPTION

Figure 1:
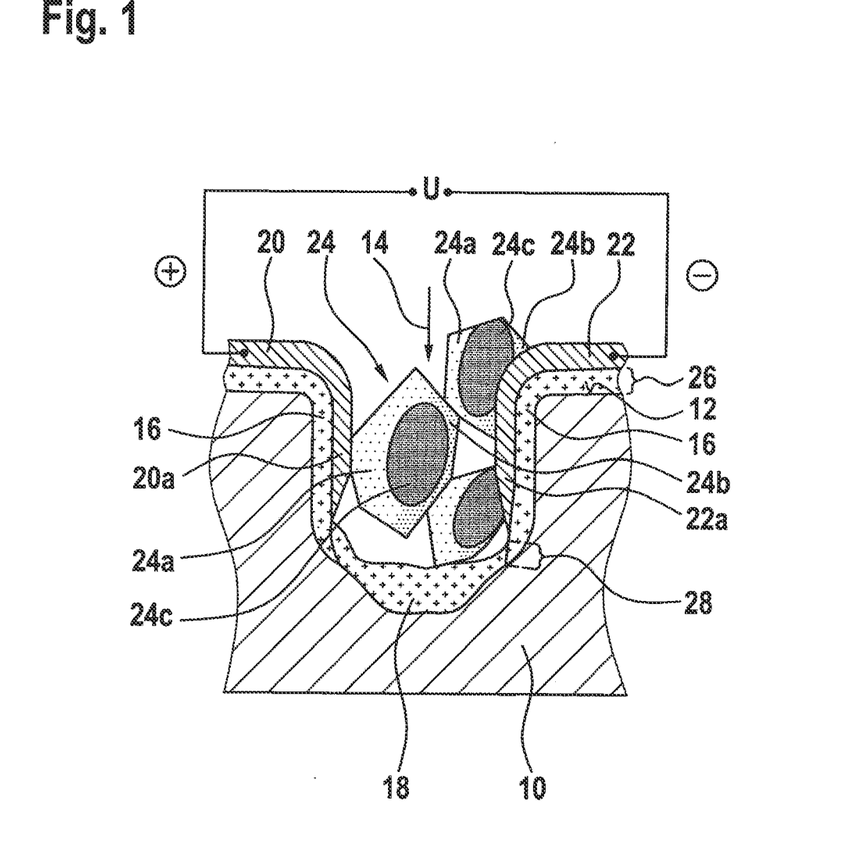
FIG. 1 shows a schematic representation of a first specific embodiment of the sensor component.

FIG. 1 shows a schematic representation of a first specific embodiment of the sensor component.

The sensor component shown schematically in FIG. 1 can be used in/on a gas and/or liquid sensor. The sensor component includes a substrate 10 having at least one trench 14 fashioned on a side 12 of substrate 10. The at least one trench 14 is fashioned having at least one trench wall 16 and at least one trench floor 18, each made of at least one electrically insulating material. Moreover, substrate 10 has at least one first printed conductor 20 and one second printed conductor 22. First printed conductor 20 and second printed conductor 22 are fashioned such that a voltage U can be applied between first printed conductor 20 and second printed conductor 22. For example, voltage U can be applied by an operating device, external to the sensor component, of the gas and/or liquid sensor. Likewise, however, a circuit (not shown) fashioned on substrate 10 can also be used to apply voltage U.

A first contact segment 20a of first printed conductor 20 and a first contact segment 22a of second printed conductor 22 are situated on two inner side surfaces, at a distance from one another, of the at least one trench wall 16 (of the same trench 14). Thus, voltage U can also be applied between contact segments 20a and 22a in the interior of the respective trench 14. At least one sensitive semiconductor material in the form of at least one particle, grain, and/or crystal 24 is filled into the at least one trench 14, at least between the at least one first contact segment 20a of first printed conductor 20 and first contact segment 22a of second printed conductor 22. Examples for the at least one sensitive semiconductor material are named below.

The above-described embodiment of the sensor component ensures an advantageous sensitivity in the detection of at least one material in a gaseous and/or liquid medium present in the at least one trench 14. The detection of the at least one material can be understood as a detection of the at least one material, a measurement of its concentration in the gaseous and/or liquid medium, and/or a determination of at least one chemical and/or physical property of the gaseous and/or liquid medium. In all cases, a good degree of sensitivity is possible in the use of the sensor component. This is explained in the following, and as an example it is assumed that via voltage U first contact region 20a of first printed conductor 20 is used as anode, and first contact region 22a of second printed conductor 22 is used as cathode. The valence electrons of the at least one sensitive semiconductor material are in this case drawn from first contact region 20a of first printed conductor 20. In the at least one particle, grain, and/or crystal 24, in the at least one trench 14 there is thus formed a first zone 24a that is enriched with electrons. At a distance from first zone 24a there is also formed in each case a second zone 24b in the respective particle, grain, or crystal 24, which has a lower electron density than an intermediate zone 24c situated between first zone 24a and associated second zone 24b. While first zone 24a is situated closer to first contact region 20a of first printed conductor 20, second zone 24b is oriented to first contact region 22a of second printed conductor 22.

Thus, due to their surface charges under the influence of contact regions 20a and 22a with applied voltage U, Schottky barriers thus occur on the at least one particle, grain, and/or crystal 24 of the sensitive semiconductor material. Moreover, the Schottky barriers can be tuned by reinforcing the depletion thickness of the surface of the particle, grain, and/or crystal 24. In this way, a zone having fewer charge barriers is also possible.

This results in a highly sensitive region close to the surface of the respective particle, grain, or crystal 24, in which even low concentrations of particular molecules can contribute to a significant change in a resistance present between contact regions 20a and 22a of printed conductors 20 and 22. Oxidative materials, such as for example $NO_2$ or ozone, attract electrons and therefore contribute to an increase in the resistance present between contact regions 20a and 22a. In contrast, other materials, in particular combustion gases, have the opposite effect, and therefore reduce the resistance present between contact regions 20a and 22a.

In general, the resistance present between contact regions 20a and 22a of printed conductors 20 and 22 is significantly lower than in the case of a conventional sensor structure having a complete sensitive semiconducting layer between two contacts. In particular, the resistance of an individual particle, grain, and/or crystal 24 of the at least one sensitive semiconductor material is significantly lower than that of a complete sensitive semiconducting layer. In comparison to a conventional sensor structure, in the sensor component small quantities of a particular material in contact with the at least one particle, grain, and/or crystal 24 captured between contact regions 20a and 22a therefore already cause a significant change in resistance. Thus, the sensor component ensures a sensitivity in the detection of the at least one material that is significantly increased in comparison to conventional sensor components.

Voltage U applied between contact regions 20a and 22a for the operation of the sensor component can for example be between 0.1 V and 5 V. Voltage U can optionally be applied as a direct voltage or as an alternating voltage. For example, for voltage U an alternating voltage can be used having a frequency in the range from 0.1 Hz to 50 Hz, preferably between 1 Hz and 20 Hz. In this way, migration processes of metal atoms from printed conductors 20 and 22 into the regions in the crystal having Schottky barriers 24a and 24b and into the depletion zones themselves are preventable even when there is a comparatively strong electrical field between contact regions 20a and 20b. The sensor component can thus still be operated reliably even at a comparatively high temperature, for example between 200 and 400° C., although the metal atoms can easily exit at such a temperature; in particular the metal atoms can pass over into the semiconducting sensitive crystal through electromigration. This can be prevented by reversing the polarity of the operating voltage. In addition to the method with the alternating voltage, this can also take place with direct voltages whose polarity has been reversed, e.g. by a circuit that reverses the polarity of the sensor or the voltage, so that for a time T+ a positive voltage is present at sensor electrode e.g. 20, and during a time T− a negative voltage is present at sensor electrode 20. The times T+ and T− can be equally long or can have different lengths, in order to make the migration of the metal atoms into the sensitive crystal reversible for the intended purpose.

Preferably, the two inner side surfaces parallel to side 12 of substrate 10, contacted by first contact segment 20a of first printed conductor 20 and by first contact segment 22a of second printed conductor 22, are at a distance from one another that is equal to a diameter of the single particle, grain, or crystal 24 of the at least one sensitive semiconductor material filled into the respective trench, or is larger by at most a factor of three than an average diameter of the particles, grains, and/or crystals 24 of the at least one sensitive semiconductor material filled into the at least one trench 14. For example, the distance between the inner side surfaces is greater by at most a factor of 2.5, preferably at most a factor of 2, preferably at most a factor of 1.5, than the average diameter of the particles, grains, and/or crystals 24 filled into the at least one trench 14. This can be realized for example in that the at least one trench 14 is fashioned with an (almost) round cross-section parallel to side 12 of the substrate, a trench diameter being equal to the diameter of the single particle, grain, or crystal 24 filled into the respective trench 14, or being a larger by at most a factor of 3, preferably at most a factor of 2.5, in particular at most a factor of 2, preferably at most by a factor of 1.5, than the average diameter of the particles, grains, and/or crystals 24 filled into the at least one trench 14. The at least one trench 14 can have a corresponding width and a depth of e.g. 1 µm. The depth of the at least one trench 14 is however relatively freely determinable. As explained below in more detail, the realization of the at least one trench 14 is also not limited to a round cross-section parallel to side 12 of substrate 10.

Thus, at most ten particles, grains, and/or crystals 24 per trench 14 can be filled into the at least one trench. For example, an (average) number of from one to five particles, grains, and/or crystals 24, in particular an (average) number of two to three particles, grains, and/or crystals 24, per trench 14 can be filled into the at least one trench 14. This ensures an advantageously increased sensitivity of the sensor component in comparison with conventional sensor components. Here, the smallest volume unit of the trench for which this enumeration is applied is a segment of this trench in which the cross-sectional surface of the trench is multiplied by the diameter of approximately 50-85% of the filled particles.

At least one surface-active glued and/or adhesive bond can be formed between a roughened surface of first contact segment 20a of first printed conductor 20 and at least one particle, grain, and/or crystal 24, contacted thereby, of the at least one sensitive semiconductor material, and/or between a roughened surface of first contact segment 22a of second printed conductor 22 and at least one particle, grain, and/or crystal 24, contacted thereby, of the at least one sensitive semiconductor material.

This ensures an advantageous hold of the respective particle, grain, and/or crystal 24 in the at least one trench 14 and a good contact between the respective contact segment 20a and 22a and the at least one particle, grain, and/or crystal 24 contacted thereby. The at least one sensitive semiconductor material can also be present in the form of sol-gel particles that are thermally treated and have few or no edges.

An average diameter of the at least one particle, grain, and/or crystal 24 can be between 10 nm and 5 µm. It is to be noted that the average diameter of the at least one particle, grain, and/or crystal 24 can be selected relatively freely. Preferably, particles are used in the 0.2 to 0.8 µm range.

The at least one sensitive semiconductor material is preferably at least one n-type semiconductor material. For example, the at least one sensitive semiconductor material can include tin oxide, zinc oxide, titanium oxide, indium oxide, and/or tungsten oxide. In order to ensure an advantageous sensitivity, the at least one sensitive semiconductor material is advantageously doped. Preferably, the doping has one valence electron more than the base material. For example, the at least one sensitive semiconductor material can be doped with tantalum and/or niobium. A concentration of the doping can be from 0.0001 mol % to 0.1 mol %, specifically from 0.0025 mol % to 0.01 mol %.

Moreover, the at least one sensitive semiconductor material can be doped with at least one alkaline earth metal and/or at least one rare earth metal. The doping with the at least one alkaline earth metal and/or the at least one rare earth metal can be present in a concentration from 0.1 to 3 mol %. Such an (additional) doping can prevent undesired crystal growth. For example, in this way crystals 24 can be grown whose average diameter is from 10 nm to 500 nm.

In order to ensure a good sensitivity to the at least one particular material, the at least one particle, the at least one grain, and/or the at least one crystal 24 of the at least one sensitive semiconductor material can also be at least partly coated with gold, silver, platinum, palladium, rhodium, and/or ruthenium. However, the materials for the coating listed here are to be understood only as examples. For example, in the detection method described here at least one receptor molecule can also be bound additionally to at least one particle, grain, and/or crystal 24.

For substrate 10, many materials, such as silicon, silicon carbide, and/or silicon nitride, can be used whose coefficient of expansion is lower than that of the at least one sensitive semiconductor material. In this way as well, an advantageous pressing of at least one particle, grain, and/or crystal 24 of the at least one sensitive semiconductor material against the at least one trench wall 16 of the at least one trench 14 can be ensured in particular when the sensor component is heated. In this way as well, a contact between printed conductors 20 and 22 and the at least one sensitive semiconductor material, as well as a good hold of the at least one particle, grain, and/or crystal 24 in the at least one trench 14, can be ensured. The at least one particle, the at least one grain, and/or the at least one crystal 24 can also be held in the at least one trench 14 by an electrical or Van der Waals force of attraction.

In the specific embodiment shown in FIG. 1, the advantageous electrically insulating realization of the at least one trench wall 16 and of the at least one trench floor 18 of the at least one trench 14 is ensured in that, after a structuring of openings in substrate 10, the at least one trench wall 16 is formed from a first insulating layer 26 and the at least one trench floor 18 is formed from a second insulating layer 28. In this way, an advantageous insulation of printed conductors 20 and 22 relative to substrate 10 is also ensured even if substrate 10 includes at least one conductive material.

Insulating layers 26 and 28 can include for example silicon nitride, silicon oxide, in particular thermal silicon oxide, and/or some other electrically insulating substance. Printed conductors 20 and 22 can be made of gold, platinum, and/or some other noble metal. Moreover, printed conductors 20 and 22 can also be impregnated with titanium, tantalum, niobium, tungsten, and/or some other metal that has a good adhesion between the covered insulating material and the metal of the printed conductors 20 and 22 applied thereon.

Figure 2:
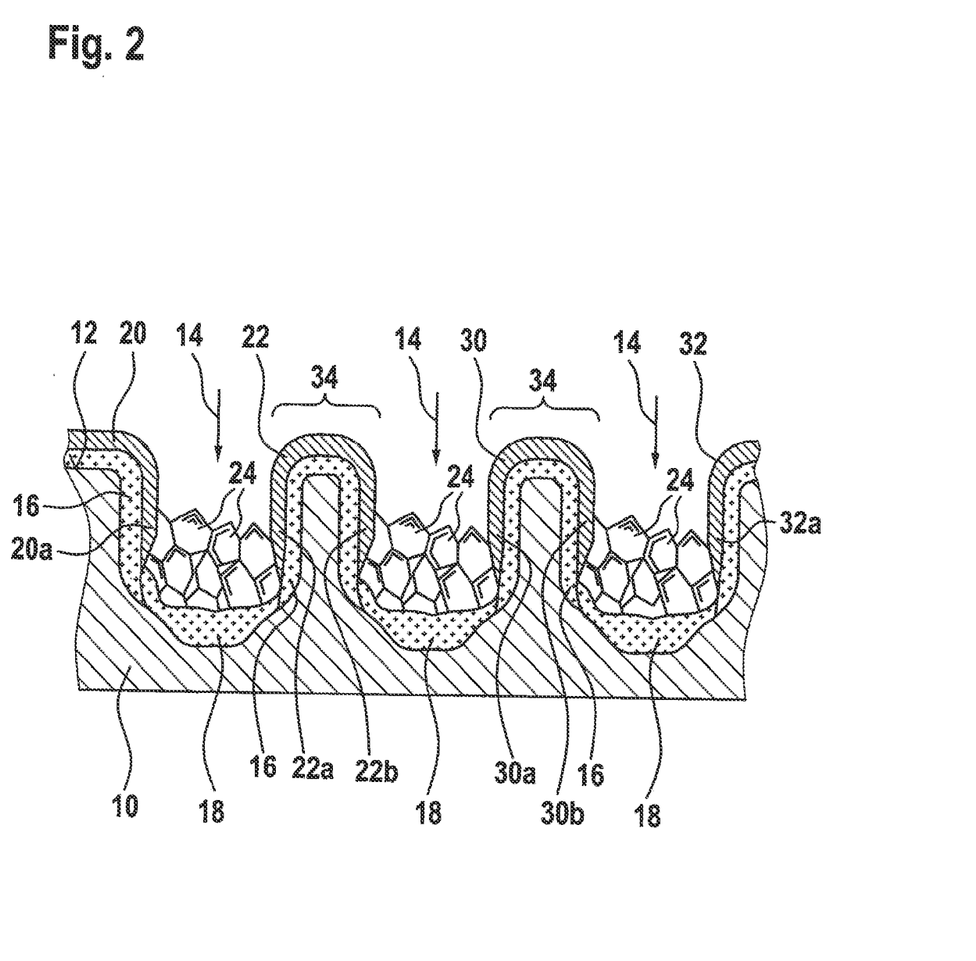
FIG. 2 shows a schematic representation of a second specific embodiment of the sensor component.

FIG. 2 shows a schematic representation of a second specific embodiment of the sensor component.

The sensor component shown schematically in FIG. 2 can be regarded as a development of the above specific embodiment. The sensor component has at least three trenches 14, each of which are, corresponding to the above specific embodiment, filled with at least one particle, grain, and/or crystal 24. The resistances realized by trenches 14 are connected in series. For this purpose, at least a third printed conductor 30 and a fourth printed conductor 32 are additionally fashioned on substrate 10. At least second printed conductor 22 and third printed conductor 30 extend over separating hills 34 fashioned between each two adjacent trenches 14. Printed conductors 22 and 30 extending over separating hills 34 each have two contact segments 22a, 22b, 30a, and 30b, each of which contacts at least one particle, grain, and/or crystal 24 in a trench 14 of the two adjacent trenches 14. Thus, via the two external printed conductors 20 and 32 having only one contact region 20a and 32a, a series circuit is realized. It can easily be seen that instead of only three trenches 14 a larger number of trenches 14 can also be connected in series in this way.

Figure 3A:
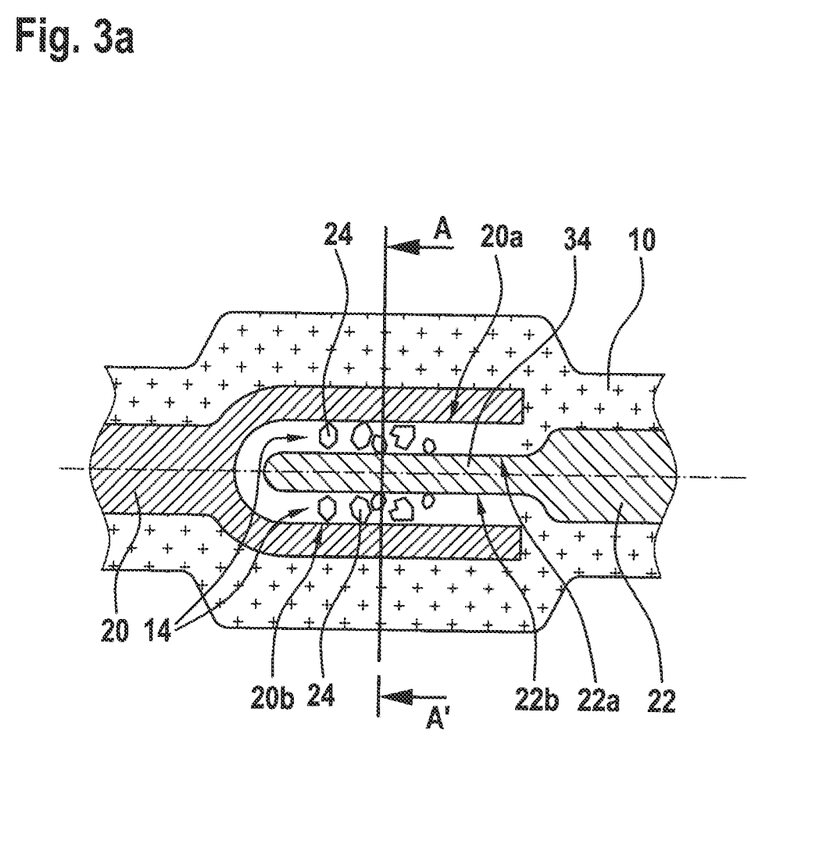
Figure 3B:
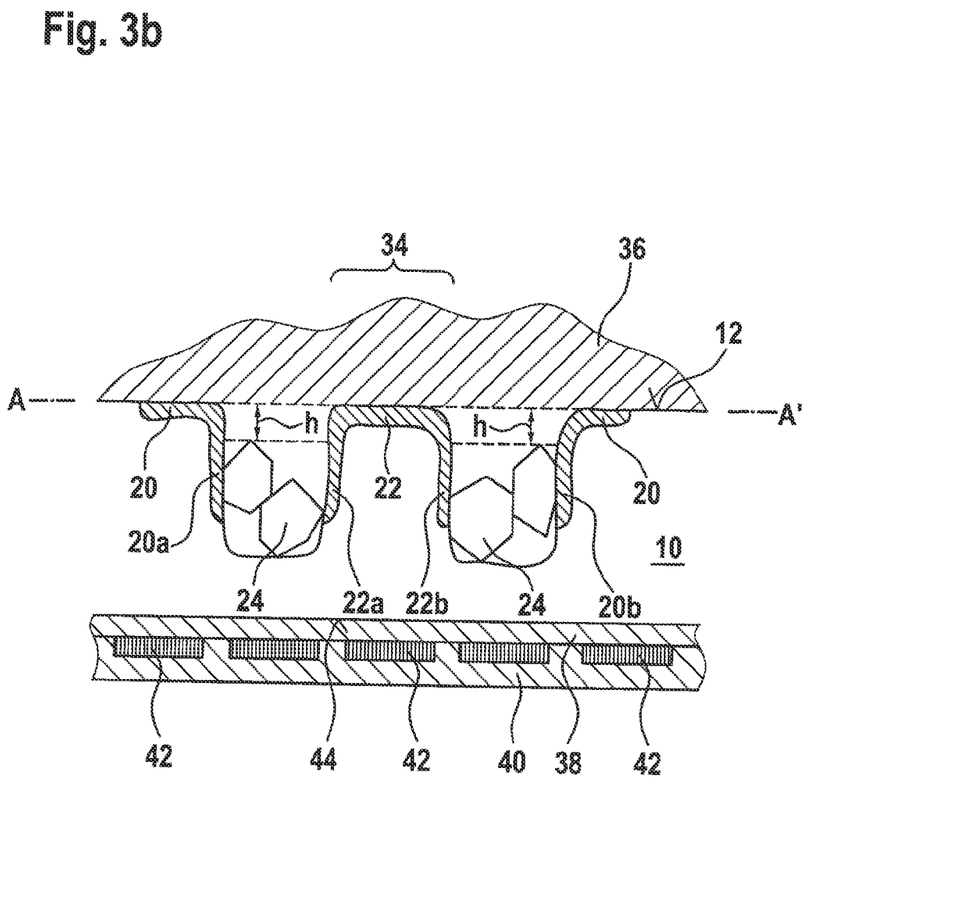

FIGS. 3a and 3b show a top view and a cross-section of a third specific embodiment of the sensor component; FIG. 3b shows a cross-section along the line A-A' of FIG. 3a.

In the specific embodiment of FIGS. 3a and 3b, the at least one trench 14 parallel to side 12 of substrate 10 has a U-shaped cross-section. The inner side surfaces having first contact segment 20a of first printed conductor 20 and first contact segment 22a of second printed conductor 22 are situated on a first limb of the U-shaped cross-section. A second contact segment 20b of first printed conductor 20 and a second contact segment 22b of second printed conductor 22 are fashioned on two further inner side surfaces, at a distance from one another, of the at least one trench wall 16 that are situated on a second limb of the U-shaped cross-section. At least one particle, grain, and/or crystal 24 is also placed between second contact segment 20b of first printed conductor 20 and second contact segment 22b of second printed conductor 22. Preferably, contact segments 22a and 22b of second printed conductor 22 are situated on a separating hill 34 that runs centrically between the two limbs of the U-shaped cross-section. This permits a comparatively simple contacting of contact segments 20a, 20b, 22a, and 22b using only the two printed conductors 20 and 22. For this purpose, first printed conductor 20 can have a fork that surrounds trench 14 at least partly. In contrast, second printed conductor 22 extends at least partly on separating hill 34. In this way, a parallel circuit of two trenches is realized that here significantly reduces the electrical resistance of the configuration by a factor of two.

As can be seen on the basis of the cross-section shown in FIG. 3b, the at least one trench 14 can also be covered by a porous protective layer 36 (not shown in FIG. 3a). The at least one porous protective layer 36 is preferably made of an electrically insulating material such as aluminum oxide. The material of the at least one porous protective layer 36 can also extend into the at least one trench 14 over a height h. The at least one porous protective layer 36 can prevent an undesired contamination of the at least one trench 14. Moreover, the at least one porous protective layer 36 also ensures a reliable hold of at least one particle, grain, and/or crystal 24 under it. The protective layer can also contain a catalyst that for example oxidizes a disturbing gas component (e.g. hydrogen, carbon monoxide) that is a disturbing factor in the detection of a second gas component such as nitrogen dioxide. Likewise, the catalyst, which is made of platinum or rhodium or one or more other noble metals or an alloy thereof, can for example oxidize nitrogen monoxide to nitrogen dioxide, which is then easier to detect.

In the cross-section shown in FIG. 3b, heating lines 42 embedded in at least one insulating layer 38 and 40 can also be seen, which are preferably fashioned on a rear side 44 of substrate 10 oriented away from side 12.

As an alternative to the fashioning of the at least one trench 14 with the U-shaped cross-section, it is also possible for only the limbs to be fashioned (as in each case a trench 14). The structuring of the connecting part can be omitted.

Figure 4:
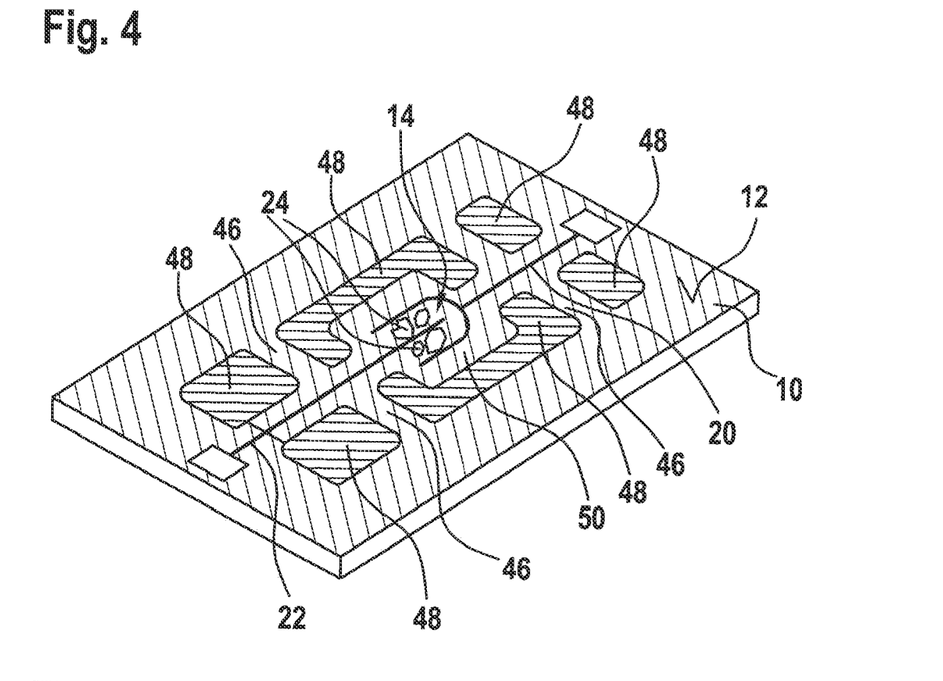
FIG. 4 shows a schematic representation of a fourth specific embodiment of the sensor component.

FIG. 4 shows a schematic representation of a fourth specific embodiment of the sensor component.

The specific embodiment of FIG. 4 can be regarded as a development of FIG. 3. Bearer structures 46 and membrane structures 48 of the at least one material of substrate 10, or at least one further material, are additionally fashioned on side 12 of substrate 10. Membrane structures 48 can for example also be made of a silicon carbide or oxygen nitride. For example, a rear-side etching can be carried out to form structures 46 and 48. Via the at least one membrane structure 48, an undesired heat transport in a direction from the at least one trench 14 to the outer regions of substrate 10 can be reliably prevented. At the same time, membrane structures 48 protect functionalized regions, situated thereunder, of the substrate from contamination. Bearer structures 46 can additionally ensure a stable hold of the substrate material region 50 surrounding the at least one trench 14.

It is to be noted that the represented realization of bearer structures 46 is to be interpreted only as an example. For example, bearer structures 46 can also have more than two arms. In a development, substrate 10 can also have at least one opening through which an air stream or liquid stream can flow. Substrate 10 can therefore be developed with a high degree of design freedom.

Figure 5A:
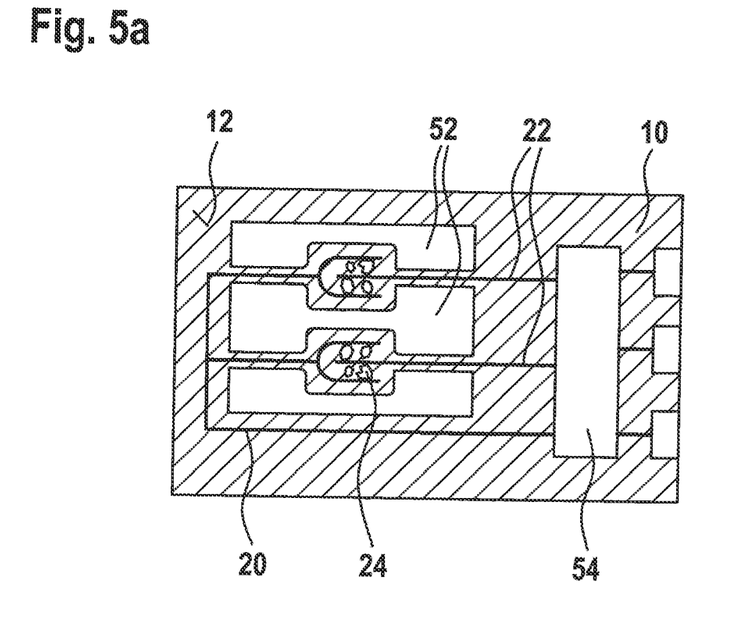
FIGS. 5a through 5c show schematic representations of a fifth specific embodiment of the sensor component.
Figure 5B:
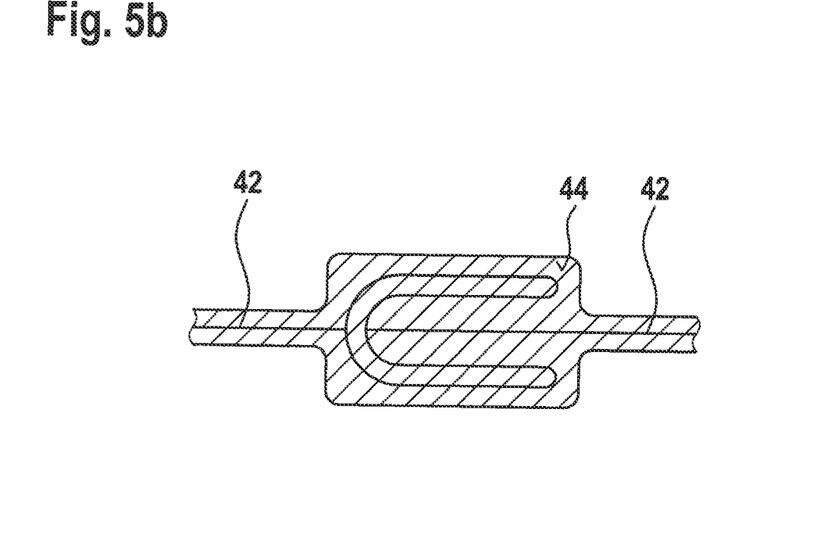
Figure 5C:
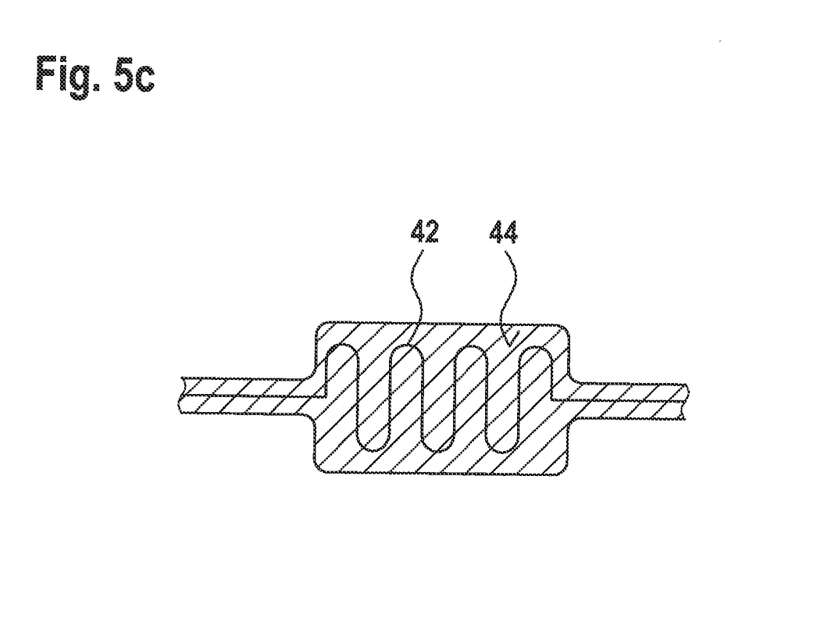

FIGS. 5a through 5c show schematic representations of a fifth specific embodiment of the sensor component.

In the specific embodiment of FIGS. 5a through 5c, two heat plates 52 are fashioned that surround the two trenches 14. A circuit 54 can also be fashioned on side 12 of substrate 10.

Moreover, FIGS. 5b and 5c show possible examples of the heating lines 42 that can be fashioned on rear side 44 of substrate 10. For example, heating lines 42 can be fashioned as a double U structure in which an outer U-shaped segment surrounds an inner U-shaped segment (FIG. 5b). Equally, heating lines 42 can cover a surface of rear side 44 of substrate 10 in meander-shaped fashion (FIG. 5c). Heating lines 42 can for example have a width and/or height from 1 μm to 3 μm. In particular, bent segments of heating lines 42 can be made wider than straight segments of heating lines 42 in order to reinforce the heating effect in a targeted manner at particular surfaces.

The advantages of the above-indicated sensor components are also ensured in a gas and/or liquid sensor having such a sensor component. Such a gas and/or liquid sensor can be used for environmental protection, to monitor the atmosphere of a living space, and/or to monitor an exhaust gas/combustion gas. Due to its comparatively low energy consumption, such a gas and/or liquid sensor can also be used in a mobile device such as a mobile telephone or a tablet, or in a computer. A use of such a gas and/or liquid sensor in a vehicle is also advantageous because, due to the small extension of the sensor components, only comparatively little energy is required for its heating, so that the energy that can be provided by the vehicle battery is adequate for the operation of the gas and/or liquid sensor.

Figure 6:
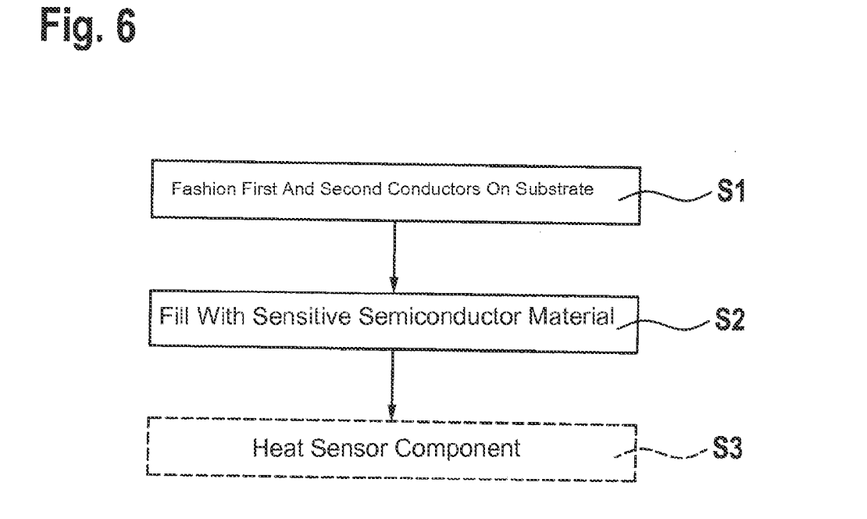
FIG. 6 shows a flow diagram explaining a specific embodiment of the production method for a sensor component for a gas and/or liquid sensor.

FIG. 6 shows a flow diagram illustrating a specific embodiment of the production method for a sensor component for a gas and/or liquid sensor.

The production method described below can be used for example to produce the above-indicated sensor components. However, the realization of the production method is limited to the production of such sensor components.

In a method step S1, at least one first printed conductor and a second conductor are fashioned on a substrate for the application of a voltage between the first printed conductor and the second printed conductor during (later) operation of the gas and/or liquid sensor. For this purpose, at least one trench is fashioned going through a side of the substrate, having at least one trench wall and at least one trench floor, each made of at least one electrically insulating material. A contact segment of the first printed conductor and a contact segment of the second printed conductor are fashioned on two inner side surfaces, at a distance from one another, of the at least one trench wall (of the same trench).

For the advantageous electrically insulating realization of the at least one trench wall and of the at least one trench floor, after a structuring of openings in the substrate, first a first insulating layer made of a first insulating material can be deposited on the whole surface on the side of the substrate on which the at least two printed conductors are formed. Subsequently, sub-areas of the first insulating layer can be removed from the floor surfaces of the openings, along with undesired excess parts of the printed conductors. For this purpose, the same etching mask can be used as is used in the formation of the openings. Subsequently, the at least one trench floor is formed by depositing a second insulating layer.

However, as an alternative to this an electrically insulating substrate can also be used to produce the sensor component. In this case it is not necessary to form the at least one trench floor and the at least one trench wall from additional insulating layers. Instead, the execution of a simple etching step is already sufficient to form the at least one trench having the at least one electrically insulating trench wall and the at least one electrically insulating trench floor. For example, an undoped and highly pure silicon substrate, a quartz substrate, and/or an electrically insulating ceramic substrate can be used for this purpose as the substrate.

To form the printed conductors, a comparatively thin coating of at least one metal and/or at least one doped semiconductor material can be deposited.

In a further method step S2, at least one sensitive semiconductor material, in the form of at least one particle, grain, and/or crystal, can be filled at least between the contact segment of the first printed conductor and the contact segment of the second printed conductor. The production of the at least one particle, grain, and/or crystal can take place in a separate chemical process, for example a crystal growth process, separately from the substrate. Thus, temperatures above 900°, which would cause damage to the substrate or to the at least one trench, can also be used during the chemical process. At least one particle, grain, and/or crystal can also be sintered. Subsequently, a coating method can be used to place at least one particle, grain, and/or crystal into the at least one trench.

In an optional method step S3, the sensor component (after the filling of the at least one particle, the at least one grain, and/or the at least one crystal made of the at least one sensitive semiconductor material into the at least one trench) can be heated to a temperature between 400° C. and 700° C. In order to further improve the hold of the at least one particle, grain, and/or crystal in the at least one trench, a sol-gel solution and/or some other conductive glue can also be deposited, for example in a spraying, sputtering, or vaporization step.

In a development, bearer structures and/or membrane structures can also be formed by etching, starting from a rear side of the substrate. A silicon nitride membrane left on the substrate can be used as an etching mask. Subsequently, the side of the bearer structure having the at least one trench can be formed. The printed conductors can then for example be laid over the silicon nitride membrane.

Figure 7:
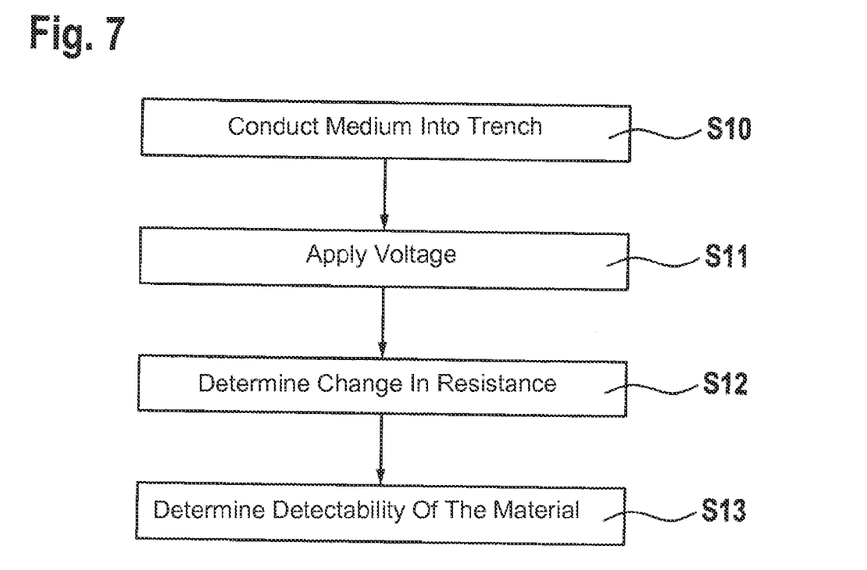
FIG. 7 shows a flow diagram explaining a specific embodiment of the method for detecting at least one material in a gaseous and/or liquid medium.

FIG. 7 shows a flow diagram illustrating a specific embodiment of the method for detecting at least one material in a gaseous and/or liquid medium.

The method for detecting at least one material in a gaseous and/or liquid medium can for example be carried out using the above-described sensor components. However, the realization of the method for detecting at least one material in a gaseous and/or liquid medium is not limited to the use of such sensor components.

In a method step S10, the medium is conducted into at least one trench going through a side of a substrate. The trench is fashioned with at least one trench wall and at least one trench floor, each made of at least one electrically insulating material. In the trench there are present, at two inner side surfaces at a distance from one another of the at least one trench wall, a contact segment of a first printed conductor and a contact segment of a second printed conductor, at least one sensitive semiconductor material, in the form of at least one particle, grain, and/or crystal, being filled into the at least one trench at least between the contact segment of the first printed conductor and the contact segment of the second printed conductor. With regard to the shapes and materials of the at least one trench and of the at least one particle, grain, and/or crystal, reference is made to the above statements.

An application of a voltage between the first printed conductor and the second printed conductor takes place in a method step S11. At the same time, in a method step S12 a quantity is determined relating to a change in resistance that occurs between the contact segment of the first printed conductor and the contact segment of the second printed conductor.

In a method step S13, taking into account the determined quantity, a detectability is determined of the at least one material in the gaseous and/or liquid medium, a concentration is determined of the at least one material in the gaseous and/or liquid medium, and/or at least one chemical and/or physical property of the gaseous and/or liquid medium is determined.

What is claimed is:

1. A sensor component for a sensor that senses at least one of a gas and a liquid, comprising:
   a substrate including at least one first printed conductor and a second printed conductor that are fashioned in such a way that a voltage can be applied between the first printed conductor and the second printed conductor;
   at least one sensitive semiconductor material present between a first contact segment of the first printed conductor and a first contact segment of the second printed conductor; and
   at least one trench arranged on a side of the substrate, the trench including at least one trench wall and at least one trench floor made of at least one electrically insulating material, wherein:
   the first contact segment of the first printed conductor and the first contact segment of the second printed conductor are situated on two inner side surfaces, at a distance from one another, of the at least one trench wall, and
   the at least one sensitive semiconductor material, in the form of at least one of a particle, a grain, and a crystal, being filled into the at least one trench at least between the first contact segment of the first printed conductor and the first contact segment of the second printed conductor.

2. The sensor component as recited in claim 1, wherein:
   the two inner side surfaces parallel to the side of the substrate are contacted by the first contact segment of the first printed conductor and by the first contact segment of the second printed conductor, and
   the two inner side surfaces are separated from one another by a distance that is one of:
      equal to a diameter of one of a single particle, grain, and crystal of the at least one sensitive semiconductor material filled into the respective trench, and
      larger by at most a factor of 3 than an average diameter of the at least one of the particle, grain, and crystal of the at least one sensitive semiconductor material filled into the at least one trench.

3. The sensor component as recited in claim 1, wherein at most a number of ten of at least one of particles, grains, and crystals per trench are filled into the at least one trench.

4. The sensor component as recited in claim 1, further comprising:
   at least one of at least one surface-active glue and an adhesive bond disposed at least one of:
      between a roughened surface of the first contact segment of the first printed conductor and at least one of the particle, grain, and crystal, contacted thereby, of the at least one sensitive semiconductor material, and
      between a roughened surface of the first contact segment of the second printed conductor and at least one of the particle, grain, and crystal, contacted thereby, of the at least one sensitive semiconductor material.

5. The sensor component as recited in claim 1, wherein the at least one sensitive semiconductor material includes at least one of tin oxide, zinc oxide, titanium oxide, indium oxide, and tungsten oxide.

6. The sensor component as recited in claim 1, wherein the at least one sensitive semiconductor material is doped with at least one of tantalum and niobium.

7. The sensor component as recited in claim 1, wherein the at least one sensitive semiconductor material is doped with at least one of at least one alkaline earth metal and at least one rare earth metal.

8. The sensor component as recited in claim 1, wherein the at least one of the particle, the grain, and the crystal of the at least one sensitive semiconductor material is at least partly coated with at least one of gold, silver, platinum, palladium, rhodium, and ruthenium.

9. The sensor component as recited in claim 1, wherein:
   the at least one trench parallel to the side of the substrate includes a U-shaped cross-section,
   the inner side surfaces having the first contact segment of the first printed conductor and having the first contact segment of the second printed conductor are situated on a first limb of the U-shaped cross-section, and
   a second contact segment of the first printed conductor and a second contact segment of the second printed conductor are disposed at a distance from one another on two other inner side surfaces of the at least one trench wall, the two other inner side surfaces being situated on a second limb of the U-shaped cross-section.

10. A sensor for sensing at least one of a gas and a liquid, comprising:
   a sensor component that includes:
      a substrate including at least one first printed conductor and a second printed conductor that are fashioned in such a way that a voltage can be applied between the first printed conductor and the second printed conductor;

at least one sensitive semiconductor material present between a first contact segment of the first printed conductor and a first contact segment of the second printed conductor; and at least one trench arranged on a side of the substrate, the trench including at least one trench wall and at least one trench floor made of at least one electrically insulating material, wherein:

the first contact segment of the first printed conductor and the first contact segment of the second printed conductor are situated on two inner side surfaces, at a distance from one another, of the at least one trench wall, and the at least one sensitive semiconductor material, in the form of at least one of a particle, a grain, and a crystal, being filled into the at least one trench at least between the first contact segment of the first printed conductor and the first contact segment of the second printed conductor.

11. A production method for a sensor component for a sensor that senses at least one of a gas and a liquid, comprising:

forming at least one first printed conductor and a second printed conductor on a substrate for application of a voltage between the first printed conductor and the second printed conductor during operation of the sensor;

situating at least one sensitive semiconductor material between the first printed conductor and the second printed conductor;

forming at least one trench, going through a side of the substrate, the trench having at least one trench wall and at least one trench floor made of at least one electrically insulating material;

forming a contact segment of the first printed conductor and a contact segment of the second printed conductor on two inner side surfaces, at a distance from one another, of the at least one trench wall; and filling the at least one sensitive semiconductor material into the at least one trench, in the form of at least one of a particle, a grain, and a crystal, at least between the contact segment of the first printed conductor and the contact segment of the second printed conductor.

12. The production method as recited in claim 11, further comprising:

heating the sensor component to a temperature between 400° C. and 700° C. after the respective filling into the at least one trench of the at least one of the particle, the grain, and the at least one crystal made of the at least one sensitive semiconductor material.

13. The production method as recited in claim 11, further comprising:

situating the sensor component at least one of in and on the sensor.

14. A method for detecting at least one material in a medium having at least one of a gas and a liquid, comprising:

conducting the medium in at least one trench going through a side of a substrate, the trench having at least one trench wall and at least one trench floor made of at least one electrically insulating material, and having a contact segment of a first printed conductor and a contact segment of a second printed conductor on two inner side surfaces, at a distance from one another, of the at least one trench wall, at least one sensitive semiconductor material being filled into the at least one trench in the form of at least one of a particle, grain, and crystal, at least between the contact segment of the first printed conductor and the contact segment of the second printed conductor;

applying a voltage between the first printed conductor and the second printed conductor;

determining a quantity relating to a change in resistance occurring between the contact segment of the first printed conductor and the contact segment of the second printed conductor; and determining at least one of:
a detectability of the at least one material in the medium,
a concentration of the at least one material in the medium, and
at least one of a chemical property and physical property of the liquid medium, taking into account the determined quantity.

\* \* \* \* \*